United States Patent
Hemmanur et al.

(10) Patent No.: US 12,178,473 B2
(45) Date of Patent: *Dec. 31, 2024

(54) UTERINE TONER DEVICE WITH BALLOON TO PREVENT AND CONTROL POSTPARTUM HEMORRHAGE

(71) Applicant: NEMOW LLC, Wheaton, IL (US)

(72) Inventors: Samartha Ram Hemmanur, Kerala (IN); Narmadha Kuppuswami, Wheaton, IL (US); Kanagasabai Muthu, Yuma, AZ (US); Periannan Sethupathi, Wheaton, IL (US)

(73) Assignee: NEMOW LLC, Wheaton, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/508,343

(22) Filed: Nov. 14, 2023

(65) Prior Publication Data
US 2024/0173051 A1    May 30, 2024

Related U.S. Application Data

(63) Continuation of application No. 18/316,557, filed on May 12, 2023, now Pat. No. 11,849,971.
(Continued)

(51) Int. Cl.
*A61B 17/42* (2006.01)
*A61B 17/12* (2006.01)

(52) U.S. Cl.
CPC ........ *A61B 17/42* (2013.01); *A61B 17/12136* (2013.01); *A61B 2017/12004* (2013.01); *A61B 2217/005* (2013.01)

(58) Field of Classification Search
CPC ............. A61B 17/12136; A61B 17/42; A61B 2017/12004; A61B 2017/4216; A61B 2217/005
See application file for complete search history.

(56) References Cited

U.S. PATENT DOCUMENTS 6,395,012 B1    5/2002  Yoon et al.
6,676,680 B1 *  1/2004  Packer ............. A61B 17/12136
                                                    607/104
(Continued)

FOREIGN PATENT DOCUMENTS

AU    2019395364 A1    6/2021
IN         409897      10/2022
WO    2020081692 A1    4/2020

OTHER PUBLICATIONS

International Searching Authority—International Search Report, pertaining to International Application No. PCT/US23/079562 dated Feb. 26, 2024, together with the Written Opinion of the International Searching Authority, 18 pages.
(Continued)

*Primary Examiner* — Ryan J. Severson
(74) *Attorney, Agent, or Firm* — Sunstein LLP

(57) ABSTRACT

Uterine toner device (UTD) for reducing postpartum hemorrhage includes: a fundal portion including a first end and a second end of the fundal portion, the fundal portion including a conical shaped tip at the first end of the fundal portion; a cervical portion including a first end and a second end of the cervical portion, the first end of the cervical portion coupled to the second end of the fundal portion, where the fundal portion and the cervical portion each include a cylindrical and tubular shaped body, where the body of the cervical portion includes a first plurality of fenestrations; and at least one balloon coupled to a surface of the cervical portion, where when the balloon is inflated, the balloon seals the cervical portion without sealing the first plurality of fenestrations.

5 Claims, 12 Drawing Sheets

RIGHT VIEW

Related U.S. Application Data

(60) Provisional application No. 63/385,184, filed on Nov. 28, 2022.

(56) References Cited

U.S. PATENT DOCUMENTS

| | | |
|---|---|---|
| 6,676,690 B2 | 1/2004 | Packer |
| 8,672,950 B2 | 3/2014 | Hahn et al. |
| 9,055,949 B2 | 6/2015 | Belfort et al. |
| 9,125,686 B2 | 9/2015 | Norred et al. |
| 9,550,014 B2 | 1/2017 | Norred et al. |
| 9,918,872 B1 | 3/2018 | Crowson et al. |
| 10,064,651 B2 | 9/2018 | Norred et al. |
| 10,315,023 B2 | 6/2019 | Mantri et al. |
| 10,722,622 B2 | 7/2020 | Loske |
| 10,813,668 B2 | 10/2020 | Isch et al. |
| 11,241,254 B2 | 2/2022 | Norred et al. |
| 11,291,473 B2 | 4/2022 | Norred et al. |
| 11,517,336 B2 | 12/2022 | Bair et al. |
| 11,583,281 B2 | 2/2023 | Roberts et al. |
| 11,849,971 B1 * | 12/2023 | Hemmanur ............ A61B 17/42 |
| 2003/0236546 A1 | 12/2003 | Packer |
| 2006/0173486 A1 | 8/2006 | Burke et al. |
| 2006/0178692 A1 | 8/2006 | Condrea et al. |
| 2008/0027421 A1 | 1/2008 | Vancelette |
| 2008/0215031 A1 | 9/2008 | Belfort et al. |
| 2013/0245581 A1 | 9/2013 | Norred et al. |
| 2013/0245637 A1 | 9/2013 | Norred et al. |
| 2014/0074110 A1 | 3/2014 | Norred et al. |
| 2017/0035949 A1 | 2/2017 | Loske |
| 2017/0281231 A1 | 10/2017 | Langell et al. |
| 2018/0055523 A1 | 3/2018 | Bair et al. |
| 2018/0264247 A1 | 9/2018 | Mantri et al. |
| 2019/0069929 A1 | 3/2019 | Isch et al. |
| 2019/0083132 A1 | 3/2019 | Norred et al. |
| 2019/0216504 A1 | 7/2019 | Norred et al. |
| 2020/0093498 A1 | 3/2020 | Roberts et al. |
| 2020/0352602 A1 | 11/2020 | Norred et al. |
| 2022/0022916 A1 | 1/2022 | Uchida et al. |
| 2022/0240982 A1 | 8/2022 | Norred et al. |
| 2022/0361891 A1 | 11/2022 | Kim et al. |

OTHER PUBLICATIONS

Pearle Study "Clinical Investigation Plan (Protocol) Pearle: Prospective, Single Arm, Pivotal Clinical Trial Designed to Assess the Safety and Effectiveness of the Jada System in Treating Primary Postpartum Hemorrhage", Version No. CIP-01 v2.6, Feb. 2019.

Vanderbilt Evidence-Based Practice Center "Management of Postpartum Hemorrhage", Comparative Effectiveness Review No. 151, Agency for Healthcare Research and Quality, Apr. 2015.

Buhimschi, Catalin S., M.D., et al., "Myometrial thickness during human labor and immediately post partum", General Obstetrics and Gynecology Obstetrics, vol. 188, Issue2, p. 553-559, Feb. 2003.

D'Alton, Mary E. M.D., et al., "Intrauterine Vacuum-Induced Hemorrhage-control Device for Rapid Treatment of Postpartum Hemorrhage", Obstetrics & Gynecology, vol. 136, No. 5, Nov. 2020.

Makhija, Bela, et. al., "Suction and Evacuation for Management of Postpartum Hemorrhage", International Journal of Women's Health and Reproduction Sciences, vol. 2, No. 5, Aug. 2014, 278-280.

Nimesh, Anjali, "S.R Vacuum Suction Cannula For The Management of Atonic PPH", https://speciality.medicaldialogues.in/s-r-vacuum-suction-cannula-for-the-management-of-atonic-pph, Dec. 28, 2017.

Panicker, T.N. Vasudeva, "Panicker's Vacuum Suction Haemostatic Device for Treating Post-Partum Haemorrhage", The Journal of Obstetrics and Gynecology of India, Mar.-Apr. 2017, 67(2): 150-151.

Hemmanur, "How to remove SR Cannula 2020", https://www.youtube.com/watch?v=sUKCEGLhRrY, Mar. 2020 (screenshot retrieved May 18, 2023).

Hemmanur, "SR Cannula Application during Caesarean section", https://www.youtube.com/watch?v=7yWrtx9cgKg, Mar. 2020 (screenshot retrieved May 18, 2023).

Hemmanur, "SR Cannula for placenta praevia 2020", https://www.youtube.com/watch?v=Elc03Ai6qGY, Mar. 2020 (screenshot retrieved May 18, 2023).

Haslinger et al., "Vacuum-Induced Tamponade for Treatment of Postpartum Hemorrage", Obstetrics & Gynecology, vol. 138, No. 3, pp. 361-365, Sep. 2021.

* cited by examiner

PERSPECTIVE VIEW

RIGHT VIEW

TOP VIEW

BOTTOM VIEW

BACK VIEW

FRONT VIEW

PERSPECTIVE VIEW

RIGHT VIEW

TOP VIEW

BOTTOM VIEW

BACK VIEW

FRONT VIEW

SECTION A-A

SECTION B-B

PERSPECTIVE VIEW

LEFT VIEW

TOP VIEW

BOTTOM VIEW

FRONT VIEW

BACK VIEW

UTERINE TONER DEVICE WITH BALLOON TO PREVENT AND CONTROL POSTPARTUM HEMORRHAGE

CROSS-REFERENCE TO RELATED APPLICATIONS

The present application is a continuation of co-pending U.S. patent application Ser. No. 18/316,557, which claims priority to U.S. Provisional Patent Application Ser. No. 63/385,184, filed Nov. 28, 2022. The foregoing application is incorporated herein by reference in its entirety.

TECHNICAL FIELD

The present invention relates to treatment of postpartum hemorrhage, and more particularly to a uterine toner device to prevent and control postpartum hemorrhage.

BACKGROUND ART

Maternal mortality and morbidity continue to be a significant problem worldwide. More than half of all maternal deaths occur either during and/or within 24 hours of giving birth. Severe bleeding in the postpartum period accounts for almost 25% of maternal deaths globally, depending on the regions and the resources. Obstetric hemorrhage is responsible for 13.4% of all maternal deaths in the US and the problem is increasing. In 2020 there were a total of 3.7 million births in the US and 140 million births globally. These mothers would face the risk of mortality or severe morbidity related to postpartum hemorrhage.

Acute hemorrhage decreases circulating blood volume. The resulting low volume triggers the sympathetic response that causes increase in systemic vascular resistance, increase heart rate, and redistribution of blood to preserve adequate blood flow to vital organs. All of these changes and the compensatory mechanisms that happen during the pregnancy help to efficiently maintain hemodynamic stability. Blood loss up to 1000 ml results only in slight changes in the clinical signs. Blood pressure is the last parameter to drop in response to bleeding. For example, a drop in the systolic blood pressure to 90 mmHg is an indication that the shock state has deteriorated from a compensatory state to a decompensatory or progressive state. This dramatic drop in blood pressure is a late finding and represents at least 30% blood loss in a healthy individual (FIG. 1). When the blood loss gets above 1000 ml, the increase in heart, respiratory rate and drop in blood pressure would be very significant and rapid. A 40% blood loss would result in hemorrhagic shock. Since drop in Blood Pressure (BP) is a late finding, relying on BP may result in the loss of time critical for effective intervention. It is very clear from the above that early intervention and prevention are the key to success in saving lives.

SUMMARY OF THE EMBODIMENTS

In accordance with one embodiment of the invention, a uterine toner device (UTD) is used to treat postpartum hemorrhage. The UTD includes a fundal portion including a first end and a second end of the fundal portion, the fundal portion including a conical shaped tip at the first end of the fundal portion; a cervical portion including a first end and a second end of the cervical portion, the first end of the cervical portion coupled to the second end of the fundal portion, where the fundal portion and the cervical portion each include a cylindrical and tubular shaped body, where the body of the cervical portion includes a first plurality of fenestrations; and at least one balloon coupled to a surface of the cervical portion, where when the balloon is inflated, the balloon seals the cervical portion without sealing the first plurality of fenestrations.

In one aspect of the UTD, the UTD further includes a tube coupled to the balloon, where liquid is injected into the balloon through the tube to inflate the balloon.

In another aspect of the UTD, inflating the balloon causes release and separation of cervical tissues drawn into the plurality of fenestrations.

In another aspect of the UTD, the UTD further includes: a vaginal portion including a first end and a second end of the vaginal portion, the first end of the vaginal portion coupled to the second end of the cervical portion; and a nipple portion including a first end and a second end of the nipple portion, the first end of the nipple portion coupled to the second end of the vaginal portion, where the fundal portion, the cervical portion, the vaginal portion, and the nipple portion each include the cylindrical and tubular shaped body, where the body of the fundal portion includes a second plurality of fenestrations, where each of the second plurality of fenestrations has a diameter that is larger than the diameter of each of the first plurality of fenestrations.

In accordance with another embodiment of the invention, a method for reducing postpartum hemorrhage includes: connecting an end of a suction tube of a pressure pump to a uterine toner device, the uterine toner device including: a fundal portion including a first end and a second end of the fundal portion, the fundal portion including a conical shaped tip at the first end of the fundal portion; a cervical portion including a first end and a second end of the cervical portion, the first end of the cervical portion coupled to the second end of the fundal portion, where the fundal portion and the cervical portion each include a cylindrical and tubular shaped body, where the body of the cervical portion includes a plurality of fenestrations; and at least one balloon coupled to a surface of the cervical portion; inflating the balloon, where the inflated balloon seals the cervical portion without sealing the plurality of fenestrations, where the inflated balloon facilitates a release of cervical tissue drawn into the plurality of fenestrations; and removing the uterine toner device.

BRIEF DESCRIPTION OF THE DRAWINGS

The foregoing features of embodiments will be more readily understood by reference to the following detailed description, taken with reference to the accompanying drawings, in which.

DETAILED DESCRIPTION OF SPECIFIC EMBODIMENTS

Embodiments of a uterine toner device (UTD) causes the uterus to contract and retract when connected to a pressure pump which creates negative pressure in the uterine cavity. The UTD causes the uterus to contract and retract, and to constrict the blood vessels in order to stop the bleeding. The UTD includes a tubular structure made of clear plastic or PVC. The UTD has varying diameters and measures approximately 24 cm in total length. The UTD includes a fundal portion of approximately 9 cm in length, a cervical portion of approximately 5 cm in length, and a vaginal portion of approximately 10 cm in length. The fundal and cervical portions have multiple fenestrations of different diameters. The fundal portion has a blunt, conical-shaped tip designed to ease the insertion of the UTD through a tight cervix. Between the fundal and cervical portions there is a visual and/or a tactile demarcation of a longer interval between the first and second plurality of fenestrations and also by a tactile ridge situated at the first end of cervical portion of the UTD which helps with the proper placement of both fundal and cervical portions of the UTD.

The musculature of the fundus which is thick (27 mm-40 mm) and contracts to push the baby down during labor. The cervical tissue is thin and soft and passively dilates to let the baby pass through. After delivery of the baby and placenta, the uterus contracts and retracts naturally to control the bleeding. But in cases of uterine atony, the fundal portion of the uterus does not contract, causing excessive bleeding. Embodiments of the UTD are used to apply negative pressure to the uterus, causing the cervical tissue to be drawn into the fenestrations of the cervical portion of the UTD. This results in a closed uterine cavity. Further continuation of negative pressure results in contraction and firm retraction of the uterus around the UTD, which stops atonic bleeding. Even following normal delivery, early application of UTD will cause contraction and early retraction of the uterus and minimize the blood loss that occurs normally. The negative pressure is maintained for a preset period of time, e.g., approximately 15 minutes. To avoid prolonged ischemia (significantly decreased blood supply), which can cause necrosis of the uterine muscle, the negative pressure is automatically discontinued at the expiration of the time period.

Figure 1:
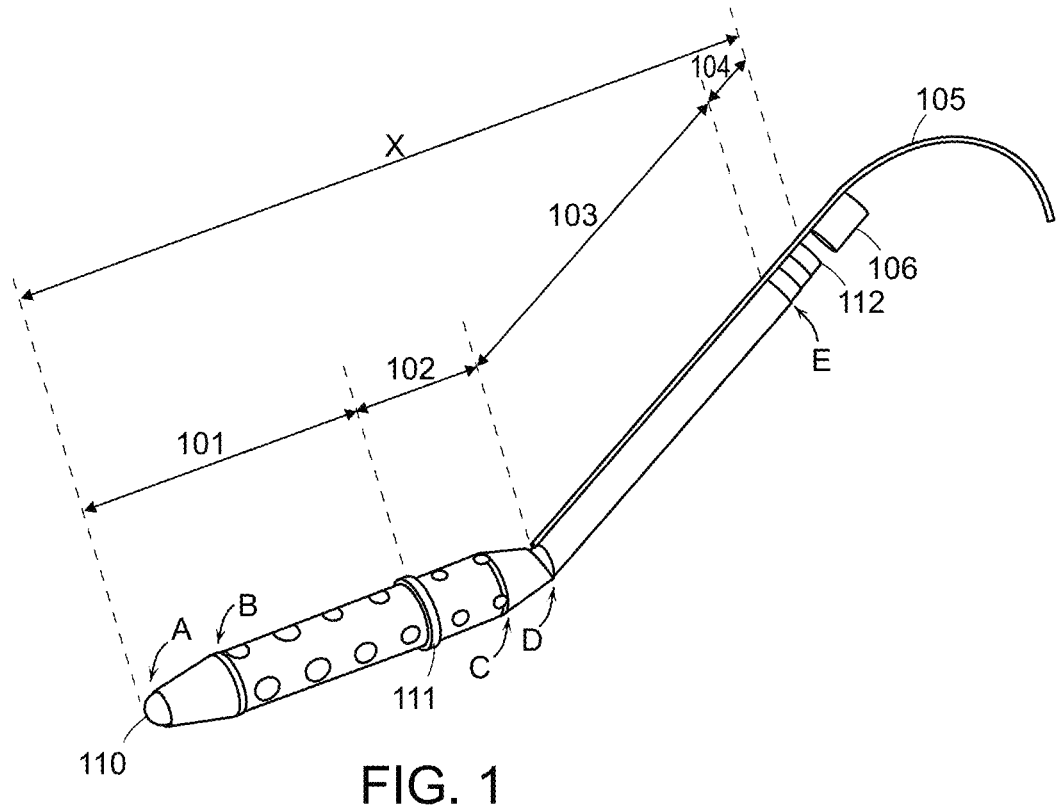
FIG. 1 illustrates a perspective view of a uterine toner device according to an exemplary embodiment of the present invention.

The Figures use the following reference numerals:
100 uterine toner device (UTD)
101 fundal portion of UTD
102 cervical portion of UTD
103 vaginal portion of UTD
104 nipple portion of UTD
105 feeding tube of the cervical balloon of the UTD
106 connector of UTD
110 tip of UTD
111 O-ring of UTD
112 end of UTD
201 first right fenestration of UTD
202 second right fenestration of UTD
203 third right fenestration of UTD
204 fourth right fenestration of UTD
205 fifth right fenestration of UTD
206 sixth right fenestration of UTD
301 first front fenestration of UTD
302 second front fenestration of UTD
303 third front fenestration of UTD
304 fourth front fenestration of UTD
305 fifth front fenestration of UTD
306 sixth front fenestration of UTD
401 first back fenestration of UTD
402 second back fenestration of UTD
403 third back fenestration of UTD
404 fourth back fenestration of UTD
405 fifth back fenestration of UTD
406 sixth back fenestration of UTD
801 inflatable balloon of UTD
1401 first left fenestration of UTD
1402 second left fenestration of UTD
1403 third left fenestration of UTD
1404 fourth left fenestration of UTD
1405 fifth left fenestration of UTD
1406 sixth left fenestration of UTD
1600 introducer
1601 tip portion of introducer
1602 body portion of introducer
1603 nipple portion of introducer
1604 dilator tip of introducer
1605 end of introducer
2201 suction tube
2202 pressure pump
2203 suction canister of pressure pump
2204 automatic shut-off switch of pressure pump
2205 pressure gauge of pressure pump
2206 pressure adjustment dial of pressure pump
2401 open uterine wound
2501 fundus
2502 upper segment of uterus
2503 lower segment of uterus
2504 cervix
2505 internal os of cervix
2506 external os of cervix
2507 vagina FIGS. 1-6 illustrate an exemplary embodiment of a uterine toner device (UTD) according to the present invention. FIG. 1 illustrates a perspective view of the UTD according to the exemplary embodiment. FIGS. 2-6 illustrate a right view, a top view, a bottom view, a back view, and a front view, respectively, of the UTD 100 according to the exemplary embodiment. The UTD 100 includes four portions: a fundal portion 101; a cervical portion 102; a vaginal portion 103, and a nipple portion 104. The four portions 101-104 include cylindrical tubular shaped bodies. In the exemplary embodiment, the total length (X) of the UTD 100 is approximately 24 cm. The length of the fundal portion 101 is approximately 9 cm from the tip 110 of the UTD 100 to the beginning of the cervical portion 102. The length of the cervical portion 102 is approximately 5 cm from the end of the fundal portion 101 to the beginning of the vaginal portion 103. The length of the vaginal portion is approximately 8.5 cm from the end of the cervical portion 102 to the beginning of the nipple portion 104. The length of the nipple portion 104 is approximately 1.5 cm from the end of the vaginal portion 103 to the end 112 of the device 100. An O-ring 111 resides between the fundal portion 101 and the beginning of cervical portion 102 to serve as a visual and tactile demarcation between them. Other types of visual demarcation may also be used. For example, the demarcation may be the longer interval between the first and second plurality of fenestrations of the UTD. The nipple portion 104 contains multiple sections of increasingly smaller diameters, with the section with the smallest diameter being the most proximate to the end 112. The UTD 100 further includes a balloon (not shown) and a tube 105 for introducing liquid into the balloon. The balloon is described further below. The UTD 100 also includes a connector 106 for coupling the UTD 100 to a suction tube (not shown).

The tip 110 of the UTD 100 has a conical shape with a rounded end. The rounded end of the tip 110 facilitates the introduction of the UTD 100 through a tight cervix with greater ease without the need for another instrument, such as a dilator. The rounded end of the tip 110 further reduces the chances of injury to the cervical tissue as compared with a sharper and bulkier end. The conical shaped tip 110 transitions to a cylindrical and tubular shaped body at point B which continues to the O-ring 111 with a substantially uniform diameter. The cylindrical and tubular shaped body continues in the cervical portion 102 from the O-ring 111 to point C with a substantially uniform diameter. At point C, the diameter of the cervical portion 102 begins to progressively narrow until the beginning of the vaginal portion 103 at point D. At point D, the vaginal portion 103 bends at approximately 145° relative to the body of the cervical portion 102 at point C, as viewed from the right side (see FIG. 2). The vaginal portion 103 has a cylindrical and tubular shaped body of substantially uniform diameter.

In the exemplary embodiment of the UTD 100, the diameter at the tip 110 is 5 mm. The diameter gradually increases from the tip 110 until point A. The diameter at point A is approximately 11 mm. The distance from the tip 110 to point A is approximately 5 mm. The diameter gradually increases from 11 mm at point A to 20 mm at point B. The diameter of the body of the fundal and cervical portions 101-102, between points B and C, is substantially uniform at approximately 20 mm. The diameter at the beginning of the vaginal portion 103, at point D, is approximately 12 mm; the diameter of the vaginal portion 103 is substantially uniform at approximately 12 mm; the diameter at the beginning of the nipple portion 104, at point E, is approximately 12 mm; and the diameter at the end 112 of the UTD 100 is approximately 10 mm. In this exemplary embodiment, the nipple portion 104 includes three rings or sections with progressively smaller diameters to increase the ease of connection to a suction tube of a pressure pump. The UTD 100 is disposable and is designed for one-time use. Possible materials for the UTD 100 include nonallergenic, latex free transparent plastic or PVC. In the exemplary embodiment, the surface of the body of the fundal and cervical portions 101, 102 contain a series of fenestrations, as described further below. Neither the vaginal portion 103 nor the nipple portion 104 contains fenestrations.

Figure 2:
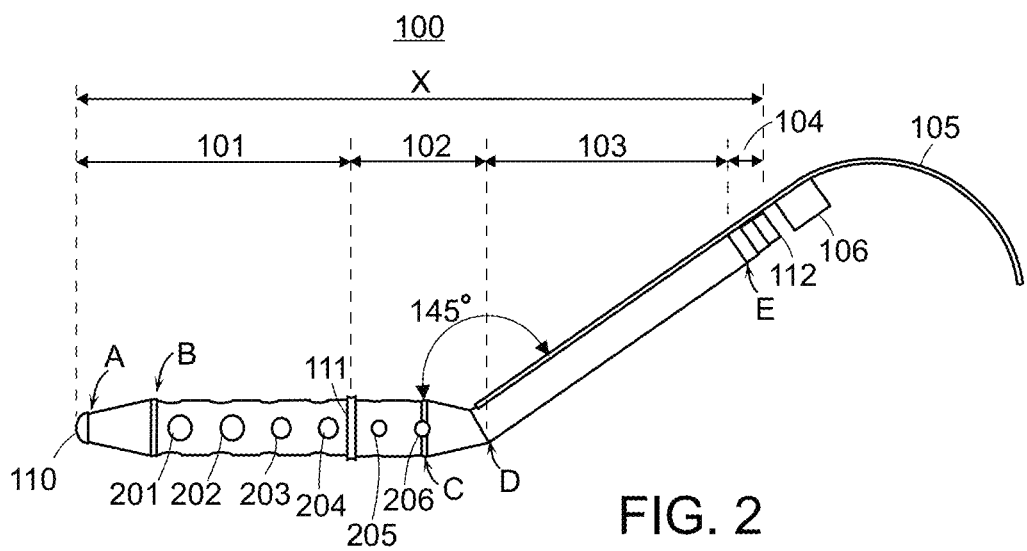
FIGS. 2-6 illustrate a right view, a top view, a bottom view, a back view, and a front view, respectively, of the uterine toner device according to the exemplary embodiment.

Referring to FIG. 2, the UTD 100 includes six fenestrations 201-206 in the right surface of the UTD 100, with four fenestrations 201-204 residing in the fundal portion 101 and two fenestrations 205-206 residing in the cervical portion 102. In the exemplary embodiment, the spacing between the fenestrations 201-206 in the right surface of the UTD 100 are as follows:

from the tip 110 to the beginning of the first right fenestration 201 is approximately 32 mm;

from the end of the first right fenestration 201 to the beginning of the second right fenestration 202 is approximately 10 mm;

from the end of the second right fenestration 202 to the beginning of the third right fenestration 203 is approximately 10 mm;

from the end of the third right fenestration 203 to the beginning of the fourth right fenestration 204 is approximately 10 mm;

from the end of the fourth right fenestration 204 to the beginning of the fifth right fenestration 205 is approximately 12 mm;

from the end of the fifth right fenestration 205 to the beginning of the sixth right fenestration 206 is approximately 10 mm; and from the end of the sixth right fenestration 206 to the beginning of the vaginal portion 103 at point D is approximately 18 mm.

The left side of the UTD 100 is a mirror of the right side. The fenestrations 1401-1406 in the left surface of the UTD 100 are visible in the longitudinal cross-sectional view of the UTD 100, illustrated in FIG. 14, described further below.

Figure 3:
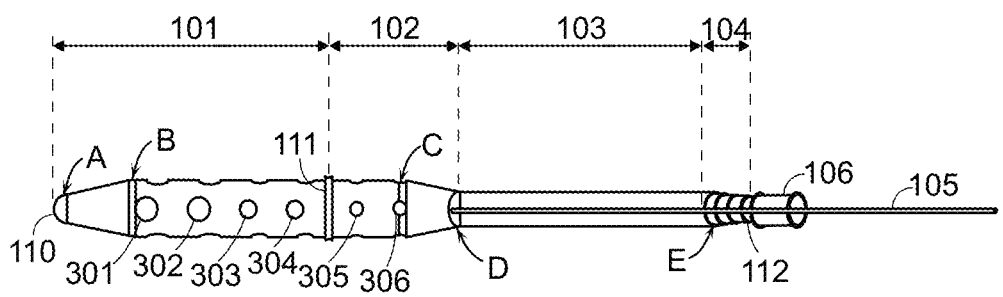

Referring to FIG. 3, the UTD 100 includes six fenestrations 301-306 in the top surface of the UTD 100, with four fenestrations 301-304 residing in the fundal portion 101 and two fenestrations 305-306 residing in the cervical portion 102. In the exemplary embodiment, the spacing between the fenestrations 301-306 in the top surface of the UTD 100 are as follows:

from the tip 110 to the beginning of the first top fenestration 301 is approximately 28 mm;

from the end of the first top fenestration 301 to the beginning of the second top fenestration 302 is approximately 10 mm;

from the end of the second top fenestration 302 to the beginning of the third top fenestration 303 is approximately 10 mm;

from the end of the third top fenestration 303 to the beginning of the fourth top fenestration 304 is approximately 10 mm;

from the end of the fourth top fenestration 304 to the beginning of the fifth top fenestration 305 is approximately 16 mm;

from the end of the fifth top fenestration 305 to the beginning of the sixth top fenestration 306 is approximately 10 mm; and from the end of the sixth top fenestration 306 to the beginning of the vaginal portion 103 at point D is approximately 18 mm.

Figure 4:
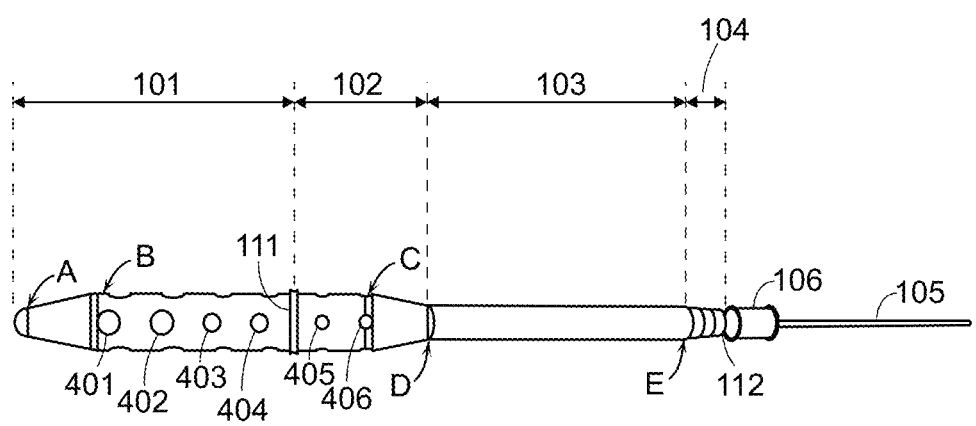

Referring to FIG. 4, the UTD 100 includes six fenestrations 401-406 in the bottom surface of the UTD 100, with four fenestrations 401-404 residing in the fundal portion 101 and two fenestrations 405-406 residing in the cervical portion 102. In the exemplary embodiment, the spacing between the fenestrations 401-406 in the bottom surface of the UTD 100 are as follows:

from the tip 110 to the beginning of the first bottom fenestration 401 is approximately 28 mm;
from the end of the first bottom fenestration 401 to the beginning of the second bottom fenestration 402 is approximately 10 mm;
from the end of the second bottom fenestration 402 to the beginning of the third bottom fenestration 403 is approximately 10 mm;
from the end of the third bottom fenestration 403 to the beginning of the fourth bottom fenestration 404 is approximately 10 mm;
from the end of the fourth bottom fenestration 404 to the beginning of the fifth bottom fenestration 405 is approximately 16 mm;
from the end of the fifth bottom fenestration 405 to the beginning of the sixth bottom fenestration 406 is approximately 10 mm; and
from the end of the sixth bottom fenestration 406 to the beginning of the vaginal portion 103 at point D is approximately 18 mm.

Figure 5:
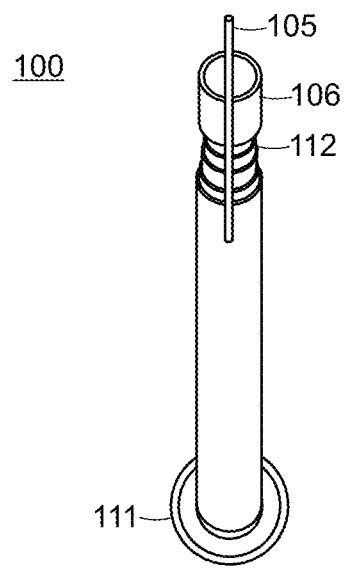
Figure 6:
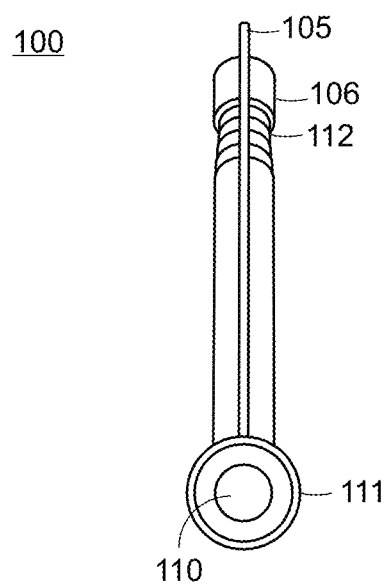

FIGS. 5 and 6 illustrate the back and front views, respectively, of the UTD 100. No fenestrations are visible in these views.

In the exemplary embodiment, the fenestrations 201-204, 301-304, 401-404, 1401-1404 comprise a first plurality of fenestrations residing in the fundal portion 101. The fenestrations 205-206, 305-306, 405-406, 1405-1406 comprise a second plurality of fenestrations residing in the cervical portion 102. The fenestrations 201-202, 301-302, 401-402, and 1401-1402 comprise a first set of the fenestrations residing in the fundal portion 101 and located proximate to the tip 110 and distal to the beginning of the cervical portion 102. The fenestrations 203-204, 303-304, 403-404, and 1403-1404 comprise a second set of the fenestrations residing in the fundal portion 101 and located distal from the tip 110 and proximate to the beginning of the cervical portion 102. In the exemplary embodiment, the diameters of the fenestrations in the first set 201-204, 301-304, 401-404, 1401-1404 are approximately 8 mm, and the diameters of the fenestrations in the second set 205-206, 305-306, 405-406, 1405-1406 are approximately 6 mm.

Further, the second plurality of fenestrations 205-206, 305-306, 405-406, 1405-1406 residing in the cervical portion 102 have diameters that are smaller than the first plurality of fenestrations 201-204, 301-304, 401-404, 1401-1404 residing in the fundal portion 101. In this exemplary embodiment, the diameters of the second plurality of fenestrations 205-206, 305-306, 405-406, 1405-1406 are approximately 5 mm.

Further, as set forth in the spacings above, the first plurality of fenestrations 201-204, 301-304, 401-404, and 1401-1404, residing in the fundal portion 101, are spaced according to a first set of distances. The second plurality of fenestrations 205-206, 305-306, 405-406, and 1405-1406, residing in the cervical portion 102, are spaced according to a second set of distances. The first plurality of fenestrations 201-204, 301-304, 401-404, and 1401-1404, residing in the fundal portion 101, are spaced according to a third distance from the second plurality of fenestrations 205-206, 305-306, 405-406, and 1405-1406, residing in the cervical portion 102. In order to provide a visual demarcation between the fundal and cervical portions 101-102 to assist the user in properly positioning the cervical portion 102 in the cervix, the third distance is greater than the first set of distances and the second set of distances. In the exemplary embodiment, as set forth above, the third distance is approximately 12 mm on the left and right surfaces, and approximately 16 mm on the top and bottom surfaces. Also in the exemplary embodiment, the O-ring 111, residing in the spacing between the first and second plurality of fenestrations residing in the fundal and cervical portions 101-102, respectively, provides an additional visual and/or tactile demarcation.

Figures 22, 23:
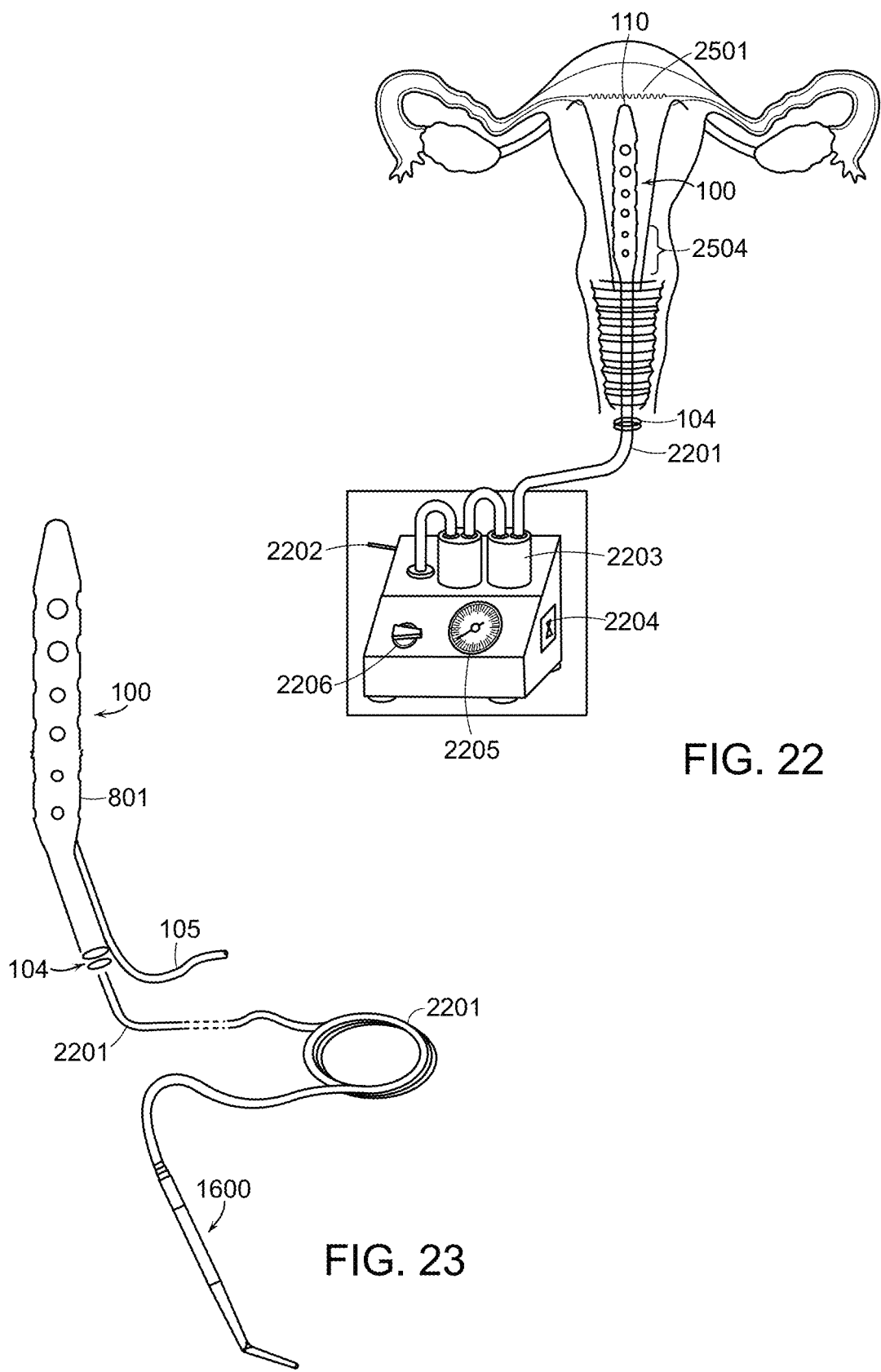
FIG. 22 illustrates the exemplary embodiment of the uterine toner device in use and connected to a pressure pump.
FIGS. 23 and 24 illustrate the combination of the uterine toner device and the introducer in use, according to an exemplary embodiment.
Figure 25:
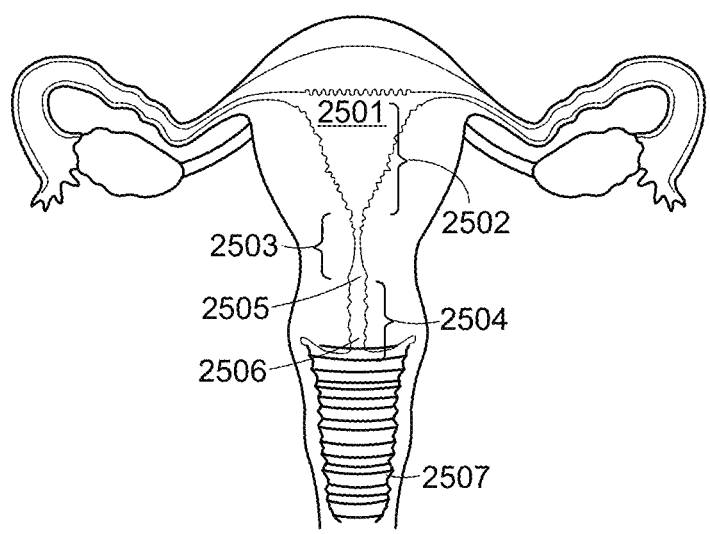
FIG. 25 illustrates the structure of the uterus, cervix, and vagina.

FIG. 22 illustrates the exemplary embodiment of the UTD in use and connected to a pressure pump. FIG. 22 includes a representation of the UTD 100 without the details of its physical features described above. As a reference, FIG. 25 illustrates the structure of the uterus, cervix, and vagina. The uterus includes the fundus 2501, the upper segment of uterus 2502, and the lower segment of the uterus 2503. Below the uterus is the cervix 2504, which includes the internal os 2505 and the external os 2506. Below the cervix 2504 is the vagina 2507. Referring to FIGS. 22 and 25, the tip 110 of the UTD 100 is inserted into the vagina 2507. The fundal portion 101 is inserted into the uterus 2503, and the cervical portion 102 is positioned within the cervix 2504. The tip 110 of the UTD 100 is positioned below the fundus 2501 without touching the fundus 2501. One end of a suction tube 2201 is connected to the end of the nipple portion 104. The opposite end of the suction tube 2201 is connected to a suction canister or bottle 2203 of a pressure pump 2202. When the pressure pump 2202 applies negative pressure to the uterus 2503 and cervix 2504, blood is removed from the uterus 2503 through the first plurality of fenestrations 201-204, 301-304, 401-404, 1401-1404 residing in the fundal portion 101, which travels through the cervical, vaginal, and nipple portions 102-104, through the suction tube 2201, and into the suction canister 2203. The pressure pump 2202 includes a pressure gauge 2205 and a dial 2206 to adjust the amount of negative pressure. In this exemplary embodiment, the pressure pump generates a negative pressure of approximately 400-650 mm of Hg. Importantly, the pressure pump 2202 includes an automatic shut off switch 2204. In the preferred embodiment, the automatic shut off switch 2204 includes a timer and automatically turns off the pressure pump 2202, releasing the negative pressure, after a pre-set amount of time, Preferably, the pressure pump 2202 applies the negative pressure for no more than 15 minutes. This will avoid prolonged ischemia (significantly decreased blood supply) which can cause necrosis of the uterine muscle.

Because the cervical tissue is thin and soft, as soon as the negative pressure is applied, the cervical tissue is drawn into the second plurality of fenestrations 205-206, 305-306, 405-406, 1405-1406 residing in the cervical portion 102 of the UTD 100. This results in a tight seal and helps to create the negative pressure in the uterine cavity. When the negative pressure reaches 650 mm Hg, the high negative pressure causes the entire uterus 2503, both the upper and lower segments, to contract and retract over the UTD 100, which stops the bleeding. Hence, it is important that the UTD 100 is properly placed, such that the cervical portion 102 of the UTD 100 is positioned in the cervical region to create a tight seal. The O-ring 111 of the UTD 100 provides a visual and/or tactile demarcation between the last fenestrations 204, 304, 404, 1404 of the fundal portions 101 and the first fenestrations 205, 305, 405, 1405, of the cervical portion 102. The O-ring 111 thus provides a visual and tactile guide to assist the user to correctly position the UTD 100 so that the cervical portion 102 is properly placed in the cervix 2504.

Uncontrollable bleeding can happen after a miscarriage, preterm delivery, in over-distended uterus like in molar pregnancy, multiple gestation, and polyhydramnios (excessive amount of amniotic fluid). In order to accommodate different obstetric bleeding situations, UTD's 100 of different sizes can be made available. The size of the UTD 100 can be selected based on the size of the uterus and the gestational period. Between the different sized UTD's, the fundal and cervical portions 101-102 would differ in lengths and diameters, while the lengths and diameters of the vaginal portions 103 would remain the same. The size and spacing of fenestrations may vary depending on the size of UTD 100, however, there would remain a distance between the first and second plurality of fenestrations in the fundal and cervical portions, respectively, to serve as a demarcation between them.

Before the use of the UTD 100, the integrity of the uterine cavity should be determined by the user performing a uterine exploration to recognize any undiagnosed uterine rupture. Such a rupture must be addressed prior to the application of the negative pressure. Otherwise, the application of the negative pressure can cause the omentum or a loop of bowel to be drawn through the rupture (defect), which can result in serious life-threatening complications.

Once the bleeding is controlled, and it is decided that the negative pressure is no longer required, the UTD 100 can be removed. In order to remove the UTD 100, the cervical tissue that was drawn into the fenestrations 205-206, 305-306, 405-406, 1405-1406 in the cervical portion 102 of the UTD 100 has to be released from the UTD 100. This release of cervical tissue can be done with a finger, using a manual digital separation method. However, since the cervical tissue is thin and soft, using digital separation could cause injury to the cervical tissue and result in bleeding. To reduce the chance of injury to the cervix, the UTD 100 may have an inflatable balloon that covers the cervical portion 102 of the UTD 100 without covering the second plurality of fenestrations.

Figure 7:
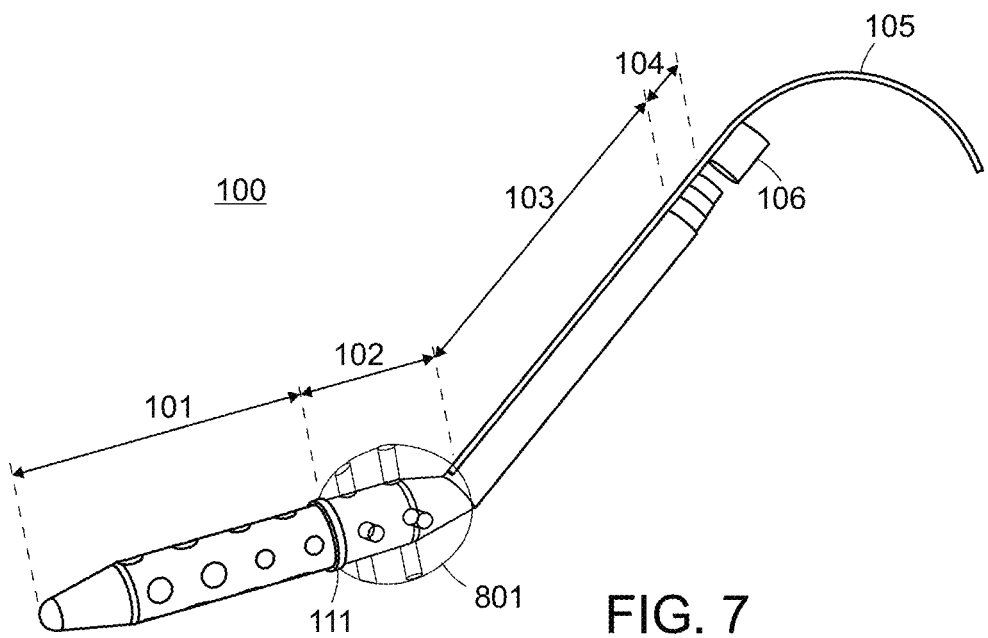
FIG. 7 illustrates a perspective view of the uterine toner device with an inflatable balloon in the inflated state, according to the exemplary embodiment.
Figure 8:
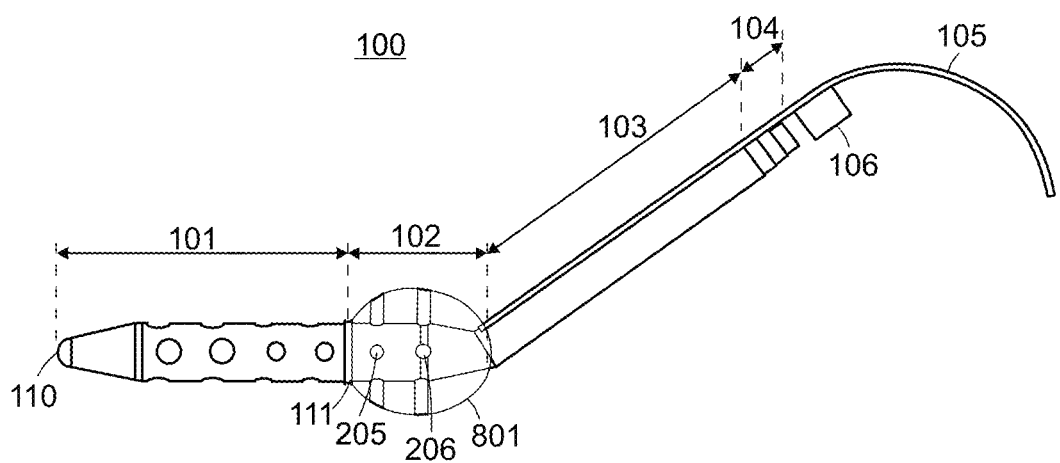
FIGS. 8-12 illustrate a right view, a top view, a bottom view, a back view, and a front view, respectively, of the uterine toner device with an inflatable balloon in an inflated state, according to the exemplary embodiment.
Figure 9:
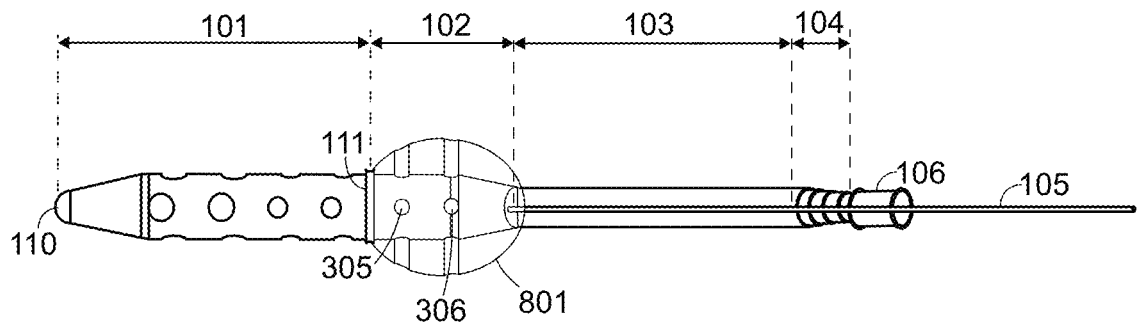
Figure 10:
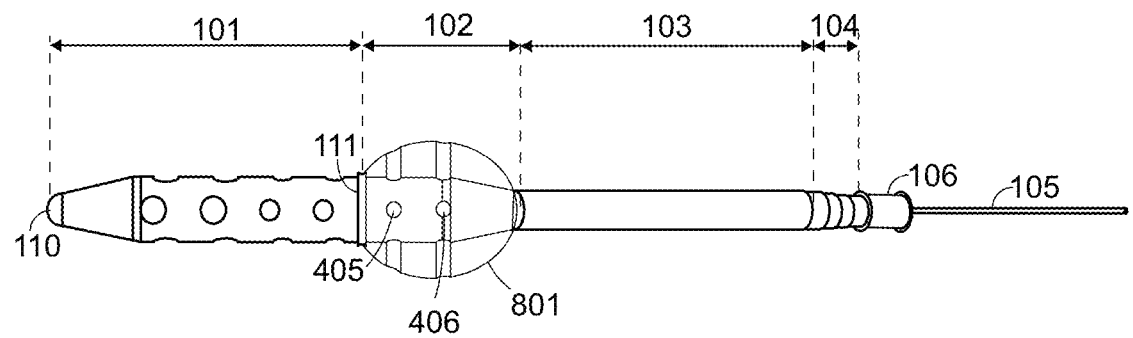
Figure 11:
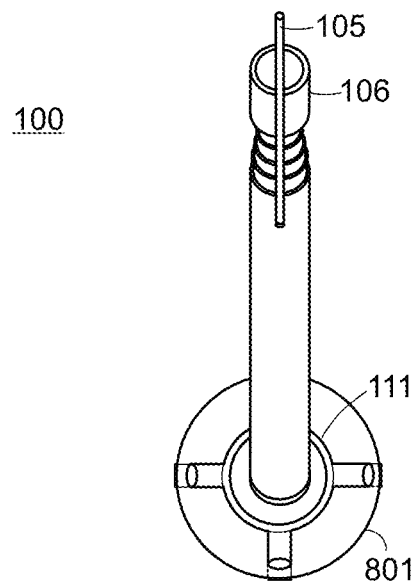
Figure 12:
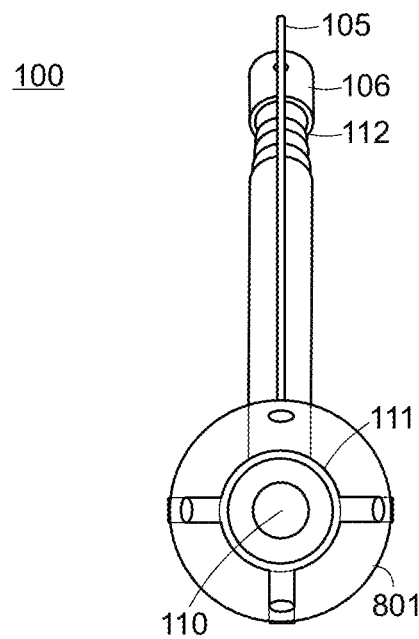
Figure 13:
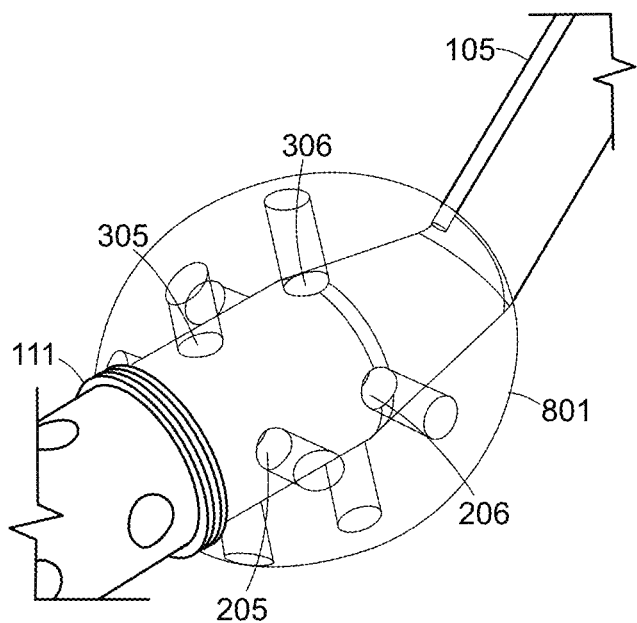
FIG. 13 illustrates a close-up view of the inflatable balloon of the uterine toner device in an inflated state, according to the exemplary embodiment.

FIGS. 7-12 illustrate the exemplary embodiment of the UTD 100 with an inflatable balloon 801 in an inflated state, according to the present invention. FIG. 7 illustrates a perspective view of the UTD 100 with an inflatable balloon 801 in the inflated state. FIGS. 8-12 illustrate a right view, a top view, a bottom view, a back view, and a front view, respectively, of the UTD 100 with an inflatable balloon 801 in an inflated state. The UTD 100 includes an inflatable balloon 801 which substantially covers the cervical portion 102. The balloon 801 may cover the area of the cervical portion 102 from the end of the fenestrations 204, 304, 404, 1404 to the beginning of the vaginal portion 103. The inflatable balloon 801 is covering the cervical portion 102 without sealing the fenestrations 205-206, 305-306, 405-406, and 1405-1406 residing in the cervical portion 102. These fenestrations 205-206, 305-306, 405-406, and 1405-1406 remain open in order to apply negative pressure to the cervix FIG. 13 illustrates a close-up view of the inflatable balloon 801 of the UTD 100 in an inflated state according to the present invention. The balloon 801 is coupled to the tube 105. The tube 105 is coupled to the top surface of the vaginal portion 103 and comes up to the nipple portion 104, and lies freely for a few centimeters, where it has a port with a stopcock (not shown). A syringe (not shown) may be used to inject liquid into the balloon 801 through the tube 105 to inflate it. For example, a liquid containing methylene blue mixed with saline is injected into the balloon 801. When the balloon 801 is inflated, it will cause gentle release and separation of the cervical tissues that were drawn into the fenestrations 205-206, 305-306, 405-406, and 1405-1406 during the application of the negative pressure. The inflation of the balloon 801 slowly, safely, and mechanically breaks the negative pressure and releases the cervical tissues from the UTD 100, making the removal of the UTD 100 easier. This helps to avoid the problems of injury to cervix and bleeding which may occur during manual digital separation. Further, any leaking of the blue mixture will alert a user of a rupture in the balloon 801. The user can then use the alternative digital separation method to release the cervical tissue from the UTD 100 before removal.

Figure 14:
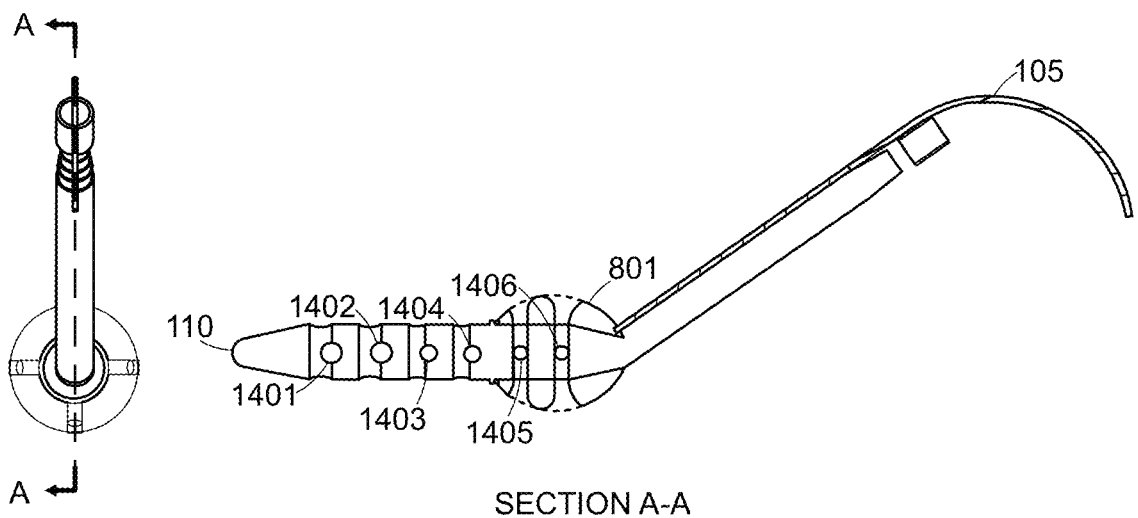
FIG. 14 illustrates a longitudinal cross-section of the uterine toner device with an inflated balloon, according to the exemplary embodiment.
Figure 15:
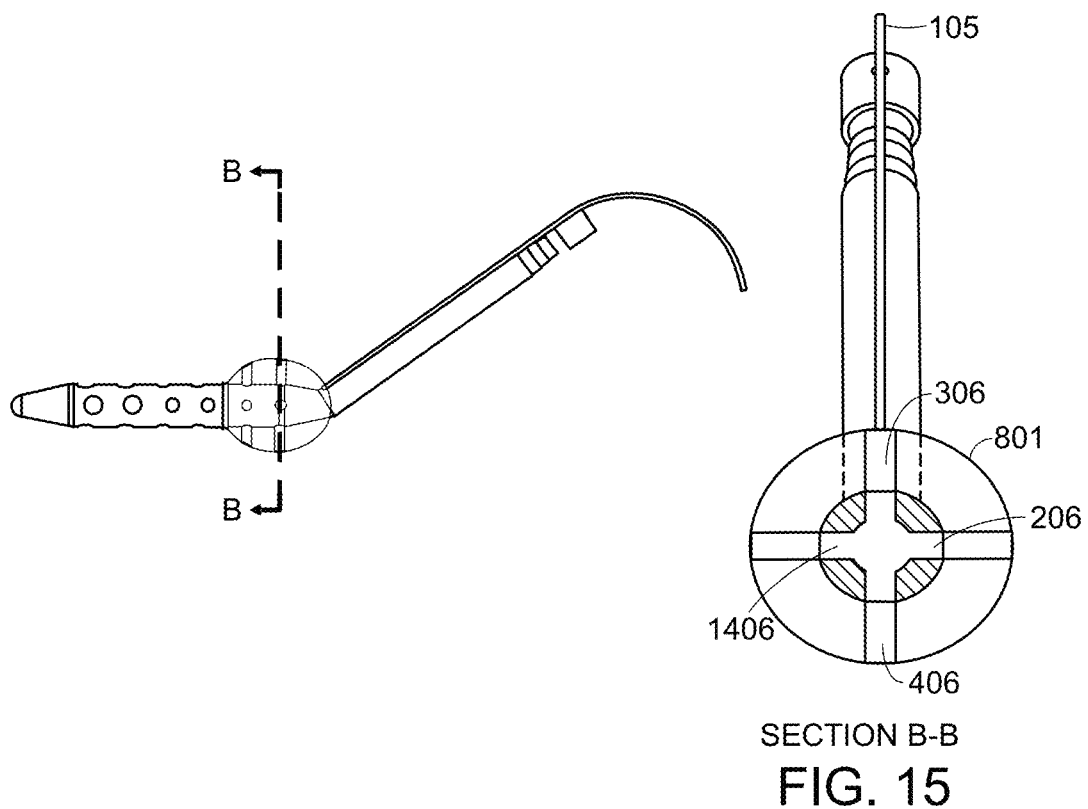
FIG. 15 illustrates a lateral cross-section of the uterine toner device with an inflated balloon, according to the exemplary embodiment.

FIG. 14 illustrates a longitudinal cross-section of the UTD with an inflated balloon, according to the present invention. FIG. 15 illustrates a lateral cross-section of the UTD with an inflated balloon, according to the present invention. In the longitudinal cross-sectional view of FIG. 14, the first through sixth fenestrations, 1401-1406 respectively, on the left wall of the UTD 100 are visible. The locations and diameters of the left fenestrations 1401-1406 mirror the right fenestrations 201-206, as set forth above. In the lateral cross-sectional view of FIG. 15, a cross section of the fenestrations 206, 306, 406, and 1406 are illustrated. The inflated balloon 801 is tethered to the edges of the fenestrations 1405 and 1406 to prevent the balloon 801 from being drawn into the fenestrations when negative pressure is applied.

The UTD 100 can be used during cesarean sections (C-Sections), i.e., the surgical delivery of a baby through an incision made in the mother's abdomen and uterus. The UTD 100 functions as a prophylaxis to prevent excessive bleeding or as a therapeutic option for uterine atony where the uterus does not contract. The UTD 100 can be used to stop excessive bleeding and prevent unnecessary blood loss. The UTD 100 is preferably assembled prior to the beginning of the C-Section procedure. The nipple portion 104 proximate to the end of the UTD 100 is coupled to a suction tube. The suction tube has to be passed through the cervix and vagina and then out of the vagina. When the C-Section is performed during labor with a dilated cervix, this process can be easy. However, when the cervix is closed, as in an elective C-section, it can be difficult to pass the suction tube through a closed tight cervix. Under these circumstances, an introducer, as described below, may be used to bring the suction tube through the vagina.

Figure 16:
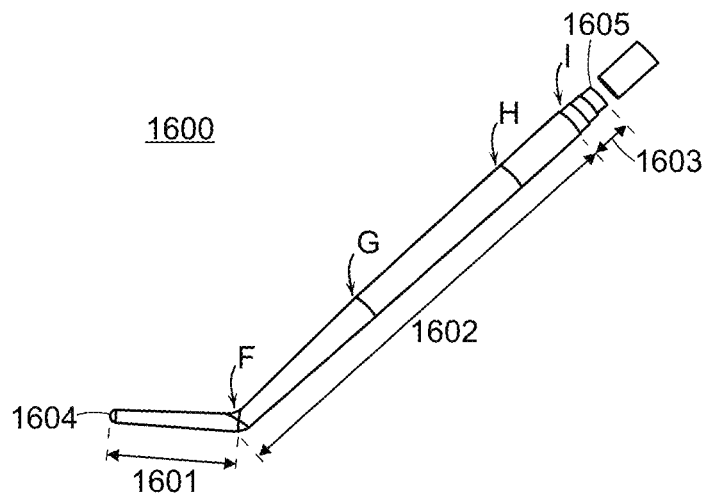
FIG. 16 illustrates a perspective view of the introducer according to an exemplary embodiment of the present invention.
Figure 17:
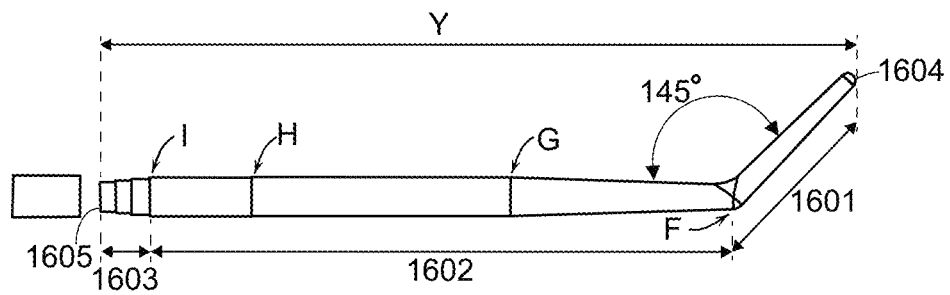
FIGS. 17-21 illustrate a left view, a top view, a bottom view, a front view, and a back view, respectively, of the introducer according to the exemplary embodiment.
Figure 18:
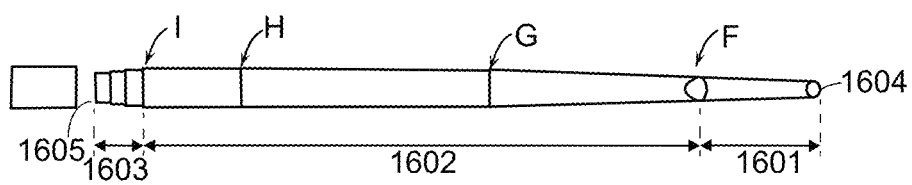
Figure 19:
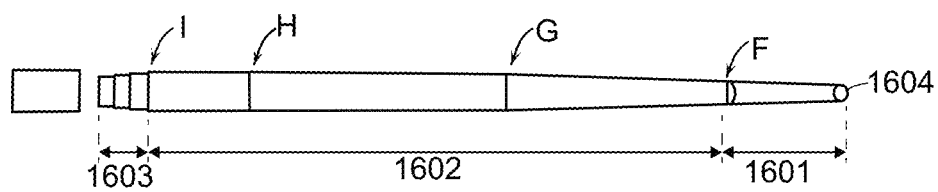
Figure 20:
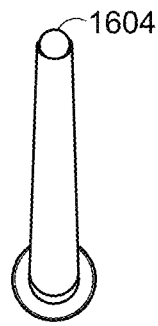
Figure 21:
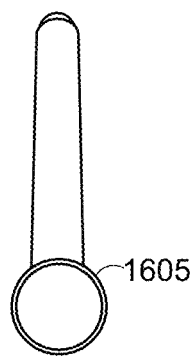

FIGS. 16-21 illustrate an exemplary embodiment of an introducer 1600 according to the present invention. FIG. 16 illustrates a perspective view of the introducer 1600. FIGS. 17-21 illustrate a left view, a top view, a bottom view, a front view, and a back view, respectively, of the introducer 1600. The right view of the introducer 1600 is a mirror of the left view. The introducer 1600 includes a tip portion 1601, a body portion 1602, and a nipple portion 1603. The total length (Y) of the introducer 1600 is approximately 25 cm. The tip portion 1601 has a conical shape with a length of approximately 5 cm from a dilator tip 1604 to a bend at point F. The body portion 1602 has a length of approximately 18.5 cm from point F to the beginning of the nipple portion 1603 at point I. The length of the nipple portion 1603, from point I to the end 1605, is approximately 1.5 cm. Similar to the nipple portion 104 of the UTD 100, the nipple portion 1603 of the introducer 1600 contains multiple sections of increasingly smaller diameters, with the section with the smallest diameter being the most proximate to the end 1605.

In the exemplary embodiment of the introducer 1600, the diameter of the tip portion 1601 gradually increases. The diameter at the dilator tip 1604 is approximately 5 mm. The diameter at the bend point (F) is approximately 7 mm. The angle of the bend is approximately 145° relative to the body portion 1602, as viewed from the left side (see FIG. 17). The diameter of the body portion 1602 also gradually increase. Point G in the body portion 1602 is approximately 7.5 cm from the bend point F, and the diameter at point G is approximately 11 mm. Point H in the body portion 1602 is approximately 15 cm from the bend point F. The body portion 1602 at point H has the maximum diameter of the introducer 1600 at approximately 12 mm. The diameter at the beginning of the nipple portion 1603 (point I) is approximately 12 mm. The diameter at the end 1605 of the introducer 1600 is approximately 10 mm.

Figure 24:
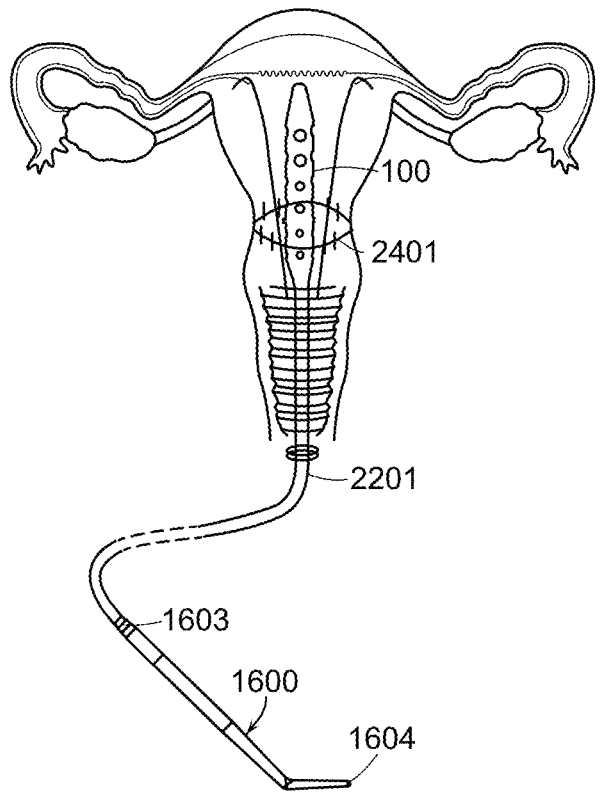

FIGS. 23 and 24 illustrate the combination of the UTD 100 and the introducer 1600 in use, according to the exemplary embodiment. In FIGS. 23 and 24, representations of the UTD 100 coupled to the introducer 1600 and in use in the uterus are provided without details of the physical features of the UTD 100 or the introducer 1600, as described above. The balloon 801 is illustrated in a deflated state. As illustrated in FIG. 23, the nipple portion 104 of the UTD 100 is coupled to one end of the suction tube 2201. The nipple portion 1603 of the introducer 1600 is coupled to the opposite end of the suction tube 2201. As illustrated in FIG. 24, the introducer 1600 is inserted through the uterine wound 2401, passed through the cervix, and then inserted into the vagina. The dilatation of a closed and tight cervix can be done slowly and progressively using the introducer as a dilator to avoid damaging the cervical tissue. Since the diameter of the introducer 1600 gradually increase from 5 mm at the dilator tip 1604 to a maximum of 12 mm, the introducer 1600 will help to dilate the cervix slowly without the need to change to different sized dilators. The dilator tip 1604 of the introducer 1600 functions as a dilator and facilitates the introducer's 1600 passage through the cervix. Since the total length of the introducer is approximately 25 cm, and the average length of a vagina is 10 cm, the introducer 1600 can pass out of the vagina without the need for the insertion of fingers into the vagina to pull out the introducer 1600. If the introducer 1600 is not visible at the vaginal opening, a surgical assistant can insert fingers through the vagina to pull the introducer 1600 out of the vagina. Once the introducer 1600 is removed from the vagina, the suction tube 2201 is disconnected from the introducer 1600 and connected to the suction canister 2203 of the pressure pump 2202 (see FIG. 22). If necessary, the surgeon adjusts the position of the UTD 100 in the uterus so that the cervical portion 102 of the UTD 100 is properly positioned in the cervix. The O-ring 111 of the UTD 100 provides visual and/or tactile assistance to the surgeon for this proper placement. The surgeon then keeps the edges of the open uterine wound 2401 close together while the surgical assistant applies negative pressure by switching on the pressure pump 2202. Due to the application of the negative pressure, the cervical tissue is drawn into the fenestrations 205-206, 305-306, 405-406, 1405-1406 in the cervical portion 102 of the UTD 100, causing a tight seal around the cervix. As the negative pressure reaches approximately 650 mm Hg, the upper and lower segments of the uterus contract and retracts around the UTD 100. This results in rapid cessation of bleeding, e.g., within 3-5 minutes. The surgeon then closes the uterine incision. The medications that are normally used to make the uterus contract and control the bleeding can be continued, as necessary. As described above with reference to FIG. 22, the negative pressure can be maintained for a maximum of 15 minutes, at which time, the pressure pump 2202 automatically shuts off, releasing the negative pressure. Though the negative pressure is released, the UTD 100 is left in situ until it is removed.

After one hour, the negative pressure can again be reapplied to a level of 650 mm Hg for another 15 minutes, and the patient can be observed for one more hour. If no further bleeding is observed after 1-3 hours, the UTD 100 can be removed. However, in the case of a postpartum hemorrhage, this process can be repeated until bleeding ceases. The UTD 100 can be left in place up to a total of 6-8 hours since the hemorrhage can recur and reintroduction of the UTD 100 may be difficult. If no further bleeding is observed after 6-8 hours, the UTD 100 can be removed. Before removing the UTD 100, about 30-40 ccs of normal saline mixed with methylene blue is injected through the tube 105 to inflate the balloon 801. As the balloon 801 is inflated, the cervical tissues that were drawn into the fenestrations 205-206, 305-306, 405-406, 1405-1406 are gradually released. Once the tissues are released, the balloon 801 can be deflated, and the UTD 100 can be easily removed.

Reference in this specification to "one embodiment", "an embodiment", "an exemplary embodiment", "some embodiments", or "a preferred embodiment" means that a particular feature, structure, or characteristic described in connection with the embodiment is included in at least one embodiment of the invention. The appearances of the phrase "in one embodiment" in various places in the specification are not necessarily all referring to the same embodiment, nor are separate or alternative embodiments mutually exclusive of other embodiments. Moreover, various features are described which may be exhibited by some embodiments and not by others. Similarly, various requirements are described which may be requirements for some embodiments but not other embodiments. In general, features described in one embodiment might be suitable for use in other embodiments as would be apparent to those skilled in the art.

It should be understood that the exemplary embodiments described herein should be considered in a descriptive sense only and not for purposes of limitation. Descriptions of features or aspects within each embodiment should typically be considered as available for other similar features or aspects in other embodiments. While one or more embodiments have been described with reference to the figures, it will be understood by those of ordinary skill in the art that various changes in form and details may be made therein without departing from their spirit and scope.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

What is claimed is:

1. A uterine toner device, comprising:
   a fundal portion comprising a first end and a second end of the fundal portion, the fundal portion comprising a conical shaped tip at the first end of the fundal portion;
   a cervical portion comprising a first end and a second end of the cervical portion, the first end of the cervical portion coupled to the second end of the fundal portion, wherein the fundal portion and the cervical portion each comprise a cylindrical and tubular shaped body, wherein the body of the cervical portion comprises a first plurality of fenestrations; and
   at least one balloon coupled to a surface of the cervical portion, wherein when the balloon is inflated, the balloon seals the cervical portion without sealing the first plurality of fenestrations.

2. The device of claim 1, further comprising:
   a tube coupled to the balloon, wherein liquid is injected into the balloon through the tube to inflate the balloon.

3. The device of claim 2, wherein inflating the balloon causes release and separation of cervical tissues drawn into the plurality of fenestrations.

4. The device of claim 1, further comprising:
   a vaginal portion comprising a first end and a second end of the vaginal portion, the first end of the vaginal portion coupled to the second end of the cervical portion; and
   a nipple portion comprising a first end and a second end of the nipple portion, the first end of the nipple portion coupled to the second end of the vaginal portion,
   wherein the fundal portion, the cervical portion, the vaginal portion, and the nipple portion each comprise the cylindrical and tubular shaped body, wherein the body of the fundal portion comprises a second plurality of fenestrations,
   wherein each of the second plurality of fenestrations has a diameter that is larger than the diameter of each of the first plurality of fenestrations.

5. A method for reducing postpartum hemorrhage, comprising:
   connecting an end of a suction tube of a pressure pump to a uterine toner device, the uterine toner device comprising:
      a fundal portion comprising a first end and a second end of the fundal portion, the fundal portion comprising a conical shaped tip at the first end of the fundal portion;
      a cervical portion comprising a first end and a second end of the cervical portion, the first end of the cervical portion coupled to the second end of the fundal portion, wherein the fundal portion and the cervical portion each comprise a cylindrical and tubular shaped body, wherein the body of the cervical portion comprises a plurality of fenestrations; and
      at least one balloon coupled to a surface of the cervical portion;
   inflating the balloon, wherein the inflated balloon seals the cervical portion without sealing the plurality of fenestrations, wherein the inflated balloon facilitates a release of cervical tissue drawn into the plurality of fenestrations; and
   removing the uterine toner device.

* * * * *